May 28, 1974 R. N. FLANAGAN Plant Pat. 3,557
APPLE TREE
Filed Jan. 8, 1973
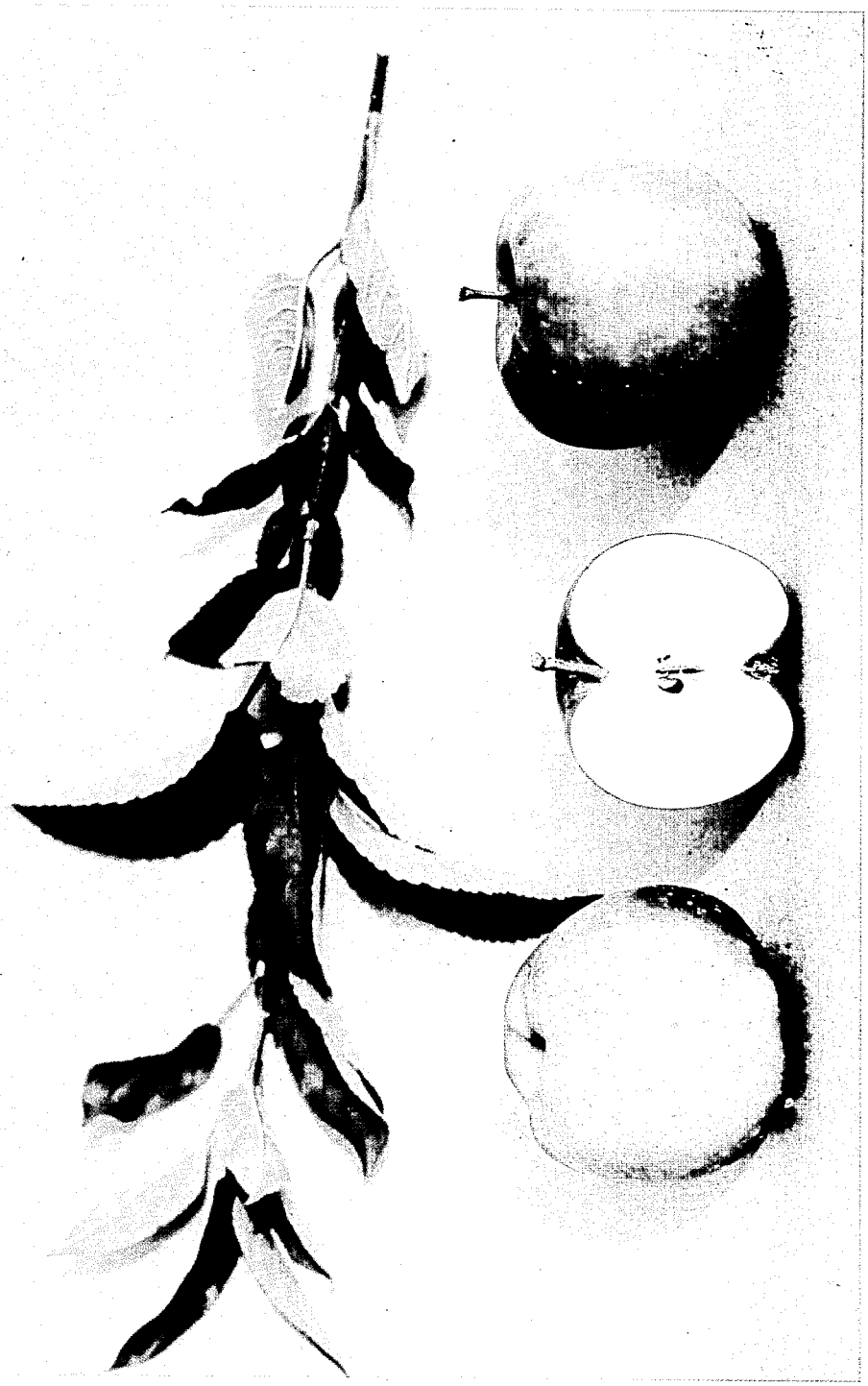

United States Patent Office

Plant Pat. 3,557

Patented May 28, 1974

3,557

APPLE TREE

Russell N. Flanagan, Thurmont, Md., assignor to Stark Bro's Nurseries & Orchards Company, Louisiana, Mo.

Filed Jan. 8, 1973, Ser. No. 321,914

Int. Cl. A01h *5/03*

U.S. Cl. Plt.—35 1 Claim

The present invention relates to a new and distinct variety of apple tree which was discovered by me as limb sport resulting from a bud mutation of the widely known apple variety of the Red Delicious type (unpatented) which has been extensively distributed and sold by the assignee hereof under the registered trademark "Starking," said discovery having been made in my cultivated orchard located at Thurmont, in the County of Frederick, Maryland.

At the time of my discovery aforementioned, I was engaged in spraying the trees in the orchard referred to above, when I noticed one limb on a particular "Starking Delicious" tree which bore red fruit while all the other fruit on the tree was green. Close inspection of this unusual limb and its fruit indicated that the tree had sported so I carefully preserved the same and kept it under continued observation. A few years later, I asexually reproduced the same by grafting in my orchard and continued my observations of both the original sport limb and its progeny derived therefrom by the graftings aforementioned. As the result of my prolonged observations and tests, which have been confirmed by experts, I am convinced that my new sport is a new and distinct apple variety, as evidenced by the following unique combination of principal characteristics which are particularly outstanding therein and which distinguish the same from its parent as well as from all other varieties of which I am aware:

(1) A spur type tree habit and a fruit form generally resembling the "Starkrimson Red Delicious" variety (Plant Pat. No. 1,565);
(2) Early-coloring fruit, with the color initially developing in a striped pattern, but becoming a brighter and lighter over-all red color sooner than the fruit of "Starkrimson Red Delicious," usually by about September first and ahead of the variety known as "Topred Delicious" (Plant Pat. No. 1,916); and
(3) An ability of the fruit to color early and well before maturity even under adverse conditions.

The accompanying drawing shows typical specimens of the foliage and fruit of my new apple variety with one of the fruit specimens being shown in cross-section, and all as depicted in color as nearly true as it is reasonably possible to make the same in a color illustration of this character.

The following is a detailed description of the new variety, with color terminology in accordance with Ridgway's Color Standards and Nomenclature [hereinafter abbreviated as (R)] and the Horticultural Color Guide [hereinafter abbreviated as (HCG)], except where general color terms of ordinary dictionary significance are obvious:

Parentage: Bud sport of "Starking Delicious."

Locality where grown and observed: Thurmont, Maryland.

Dates of first and last pickings: About Sept 20 and Oct. 5, respectively.

Tree: Medium small; vigorous; upright; dense; medium slow growing; hardy; very productive; regular bearer.

*Trunk.*—Stocky; smooth.

*Branches.*—Medium thickness; smooth; many spurs. Color—Buffy Brown, Plate XL, Color No. 17‴, tone i (R). Lenticels—Medium number; medium small.

*Leaves.*—Medium large; medium narrow; medium long; oval; taper-pointed; thick; rugose. Length—From about 3½ inches to 4 inches. Width—about 1⅞ inches. Color—Ivy Green, Plate 060/1, page 200, Vol. 2 (HCG). Margin—Coarsely serrate. Petiole—Medium long; thick.

Flowers: Medium early.

*Dates of first and full bloom*—About May 2 and May 5, respectively.

*Color.*—White, with tinge of Carmine, Plate 21/3 page 21, Vol. 1 (HCG).

Fruit:

*Maturity when described.*—Eating ripe.

*Size.*—Uniform. Axial diameter—From about 3 inches to 3⅛ inches. Transverse diameter—From about 3⅛ inches to 3¼ inches.

*Form.*—Conical; angular.

*Cavity.*—Symmetrical; flaring; undulate; pubescent toward apex. Depth—About ⅝ inch. Breadth—About 1⅜ inches. Markings—Color—Deep Grape Green, Plate XL, Color No. 25‴, tone i (R).

*Basin.*—Symmetrical; abrupt at base; wide base; furrowed; glabrous. Depth—about ⅜ inch; breadth—about ⅛ inch.

*Stem.*—Medium stout; pubescent. Length—from about ⅞ inch to 1⅛ inches; breadth—about ⅛ inch.

*Calyx.*—Closed; persistent, broadly lanceolate; acute; about ¼ inch long; approximate; prostrate; reflexed from base at apex; converged from base toward center; both inner and outer surfaces pubescent.

*Skin.*—Thick; tough; smooth; glossy; waxed. Dots—Obscure; many; small; even; ruptured; circular. Color of dots—Tilleul Buff, Plate XL, Color No. 17‴, tone f (R). Distribution—Overall, but most numerous toward basin. Ground color—Carrot Red, Plate XIV, Color No. 7′, tone b (R). Color markings—Striped at first, but becoming almost solid color; self-colored; bright. Color of markings—new Blood Red; Plate 820, page 166, Vol. 2. General color effect—Nearly solid bright red, with faint lighter red stripes.

Flesh: Juicy.

*Color.*—Satiny white, with greenish tint.

*Texture.*—Firm; fine; crisp.

*Flavor.*—Mild.

*Quality.*—Good.

Core: Median.

*Bundle area.*—Medium small; oblate; symmetrical; acute at base.

*Halves of area.*—Equal.

*Bundles.*—Inconspicuous; in one whorl. Color—Citron Green, Plate XXI, Color No. 25″, tone b (R).

*Core lines.*—Clasping.

*Cross section.*—Indistinct.

*Carpellary area*—Indistinct; small.

*Calyx tube.*—Glabrous toward base and apex; funnel-form. Stem of funnel—Short. Depth of tube to shoulder—About ⅛ inch. Entire depth—About 5/16 inch.

*Styles.*—Present; united toward base; pubescent toward apex.

*Stamens.*—In one median whorl.

*Seed cells.*—Axile; open. Cell walls—Approximate; thin; tough. Length—About 9/16 inch; breadth—about 5/16 inch. Longitudinal section—Broadly ovate; obtuse at apex. Surface—Entire. Cross section—Narrow.

Seeds: Usually 8 perfect and 1 imperfect; no more than 2 per cell.

*Length.*—About 9/32 inch.

*Breadth.*—About 3/16 inch.

*Form.*—Acute.

*Color.*—Chestnut, Plate II, Color No. 9, tone m (R).

Use: Market; dessert.

Keeping quality: Good; about 120 days in ordinary storage.

*General observations*

While my new apple variety is a bud sport of the unpatented variety "Starking Red Delicious," its tree habit and fruit form more nearly resembles that of the "Starkrimson Red Delicious" (Plant Pat. No. 1,565) than any other variety, but the fruit of the sport is much earlier coloring and becomes much brighter and lighter in color overall than the fruit of "Starkrimson Red Delicious," usually by about September first at Thurmont, Maryland. In comparison with the variety "Redspur" (Plant Pat. No. 1,822), the tree habit of the latter is genetically semi-dwarf and not quite as large as that of my new sport, and the fruit of "Redspur" is more blockly in shape and its color is yellowish-green at the calyx end, in contrast, with the overall solid bright red color of the fruit of my new variety. As compared with the variety "Sturdyspur" (Plant Pat. No. 2,433), here again the tree habit of the latter is semi-dwarf and not quite as large as my new variety, and the fruit color is a much darker red color than the bright red color of the fruit of my new variety.

I claim:

1. A new and distinct variety of apple tree, substantially as herein shown and described, characterized particularly as to novelty by the unique combination of a spur type tree habit and a fruit form generally resembling the "Red Delicious" variety (Plant Pat. No. 1,565), which has been widely distributed and sold by my assignee under the registered trademark "Starkrimson," early-coloring fruit, with the color initially developing in a striped pattern, but becoming a brighter and lighter over-all red color sooner than the fruit of "Starkrimson Red Delicious," usually by about September first and ahead of the variety known as "Topred Delicious" (Plant Pat. No. 1,916), and an ability of the fruit to color early and well before maturity even under adverse conditions.

References Cited

UNITED STATES PATENTS

| | | | |
|---|---|---|---|
| P.P. 1,565 | 2/1957 | Bisbee | Plants—35 |
| P.P. 1,822 | 3/1959 | Gilbert | Plants—35 |
| P.P. 2,433 | 8/1964 | Miller | Plants—35 |

ROBERT E. BAGWILL, Primary Examiner